United States Patent [19]

Benoit et al.

[11] Patent Number: 5,572,569
[45] Date of Patent: Nov. 5, 1996

[54] TILTING IMAGING TABLE

[75] Inventors: P. Kevin Benoit, Bath; James M. Bradcovich, Akron; Richard J. Frankovich, North Olmsted, all of Ohio

[73] Assignee: Beta Medical Products, Akron, Ohio

[21] Appl. No.: 414,373

[22] Filed: Mar. 31, 1995

[51] Int. Cl.$^6$ .................................................. A61B 6/04
[52] U.S. Cl. ............................ 378/209; 378/177; 5/610; 5/601
[58] Field of Search ............................ 378/208, 209, 378/177, 178, 179, 195, 197; 5/601, 610, 611

[56] References Cited

U.S. PATENT DOCUMENTS

| | | | |
|---|---|---|---|
| 3,631,242 | 12/1971 | Williams | 378/209 |
| 3,806,109 | 4/1974 | Weber et al. | 378/209 |
| 3,845,947 | 11/1974 | Lee | 378/209 |
| 4,452,439 | 6/1984 | Hogan | 378/209 |
| 4,905,266 | 2/1990 | Kuck et al. | 378/177 |
| 5,127,034 | 6/1992 | Wright | 378/209 |

*Primary Examiner*—Don Wong
*Attorney, Agent, or Firm*—Oldham & Oldham Co., L.P.A.

[57] ABSTRACT

An imaging table for medical examination and imaging procedures. A tilting imaging table comprises a rectangular base frame on wheels, a column extending upwardly from the base, and a tilt assembly which includes a pair of rotatable pivot arms at the top of the column. A radiolucent table top for imaging purposes is removably secured to the tilt assembly. At least two interchangeable radiolucent table tops, of different configurations and used for different medical imaging purposes, accompany the tilting imaging table and may be secured removably, one at a time, to the tilt assembly. This tilt assembly and any table mounted thereon are tiltable about a transverse axis between a head up position (e.g, 30° head up) and a head down position (e.g., 30° head down). Greater degree of tilt in one direction can be provided if desired. Also shown is a limit stop mechanism for retaining a tilting assembly including pivot arms in a horizontal position. This mechanism includes a solenoid operated swinging arm which engages a limit stop affixed to a pivot arm when the solenoid is not energized. When the solenoid is energized, a plunger and a link pivotally attached thereto are pulled downwardly against the bias of a compression spring, causing the swinging arm to be rotated out of engagement with the limit stop, so that the tilt assembly including pivot arms is free to rotate. This limit stop mechanism can be used both with the imaging table described in detail herein and with other longitudinally tiltable image tables.

16 Claims, 10 Drawing Sheets

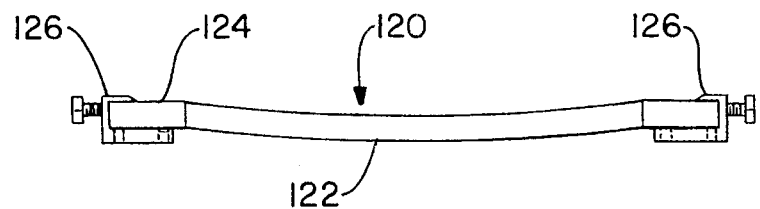
FIG.-9
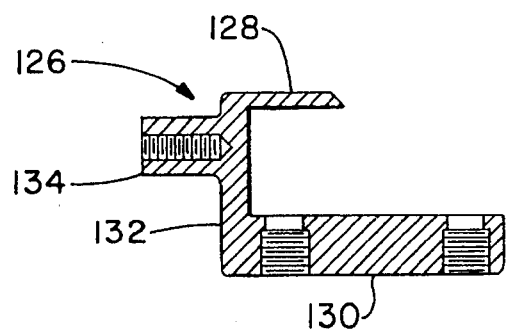
FIG.-10
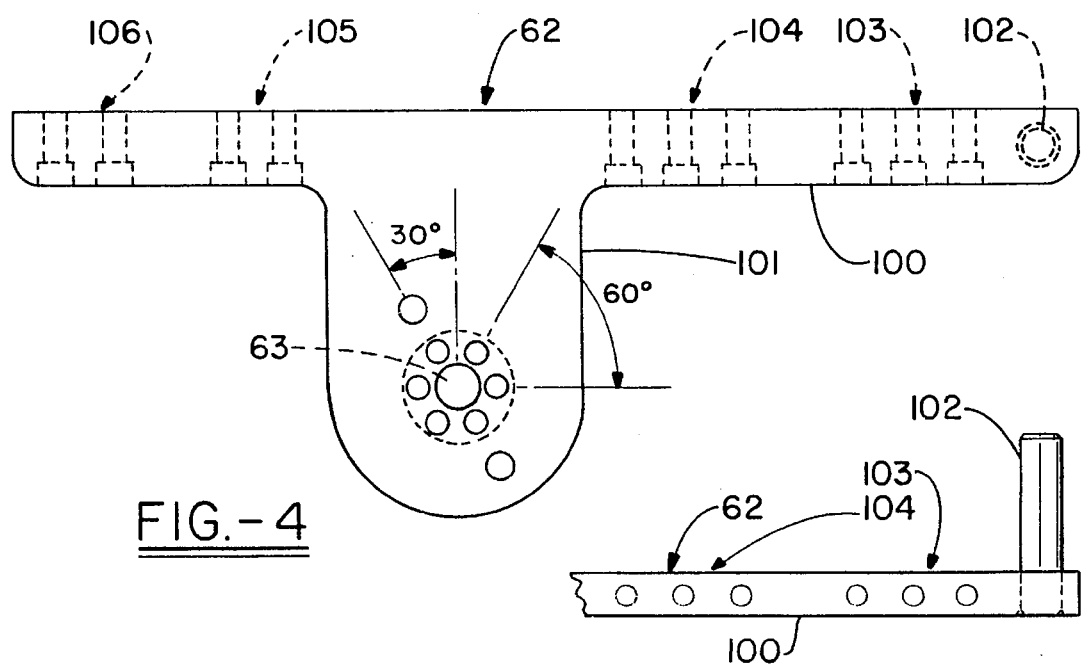
FIG.-4
FIG.-5

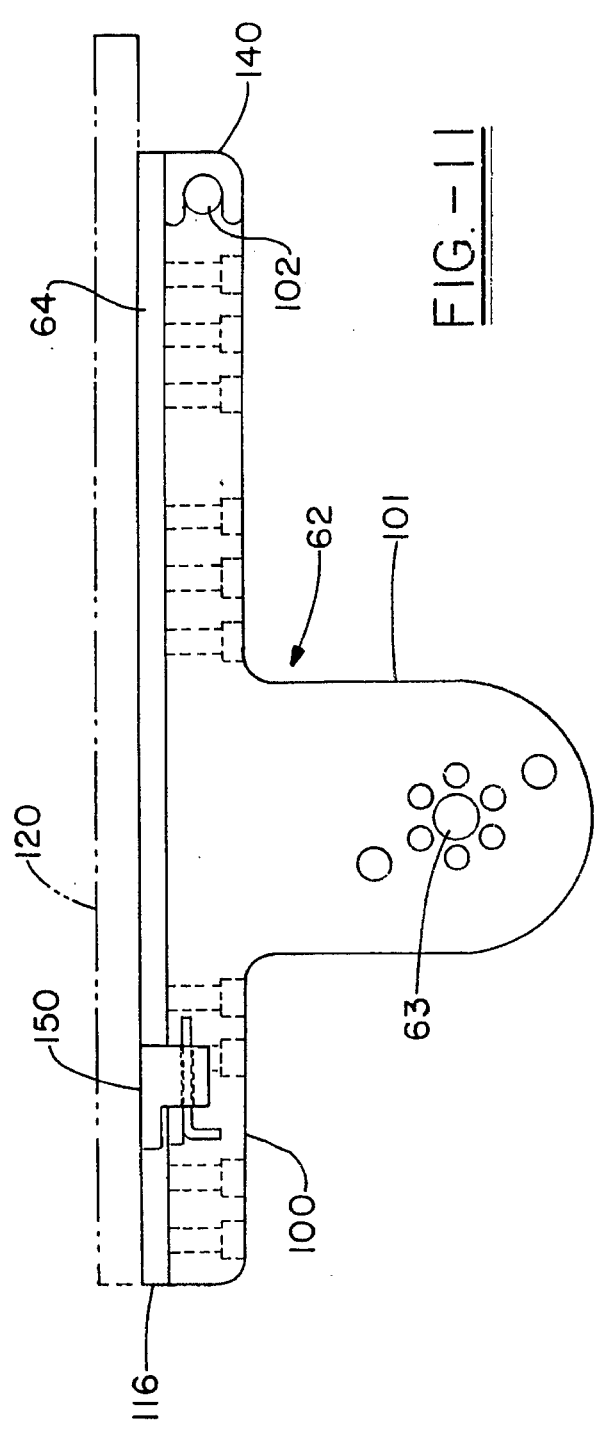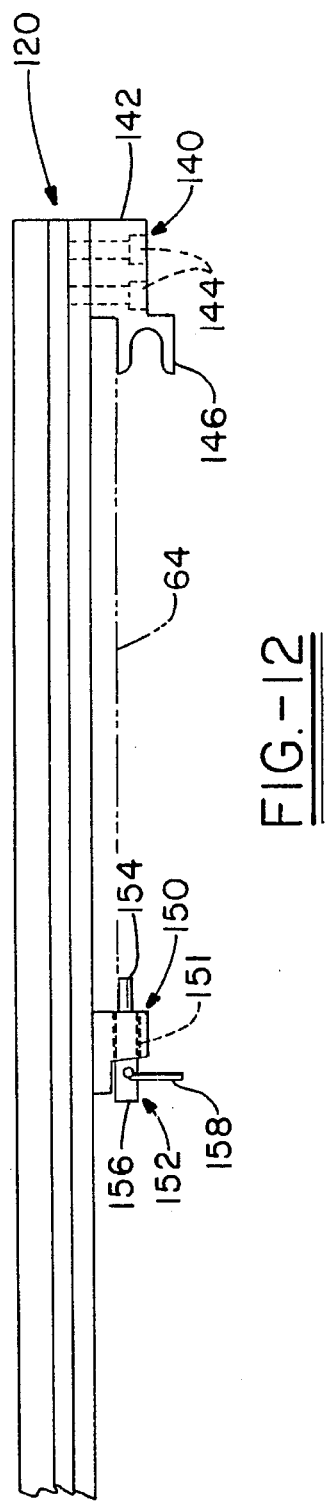

TILTING IMAGING TABLE

FIELD OF THE INVENTION invention relates to tables for medical procedures and more especially to longitudinal tiltable tables for medical imaging purposes.

BACKGROUND ART

Imaging tables for supporting a patient for medical diagnostic imaging purposes are well known. Tables of this type are shown and are described, for example, in U.S. Pat. No. 4,541,108 to Grady et al, U.S. Pat. No. 5,048,071 to Van Steenburg, and U.S. Pat. No. 5,237,600 to Kamata. These devices include a stationary base anchored to the floor of an examination room, a vertical column extending upwardly from the base, and a radiolucent table top and table top support structure extending laterally from the column, so that the patient is supported in cantilevered fashion. The table tops in all of these references can be raised and lowered. The devices shown in two of these patents, i.e., U.S. Pat. No. 4,541,108 and U.S. Pat. No. 5,048,071, also permit the table top to be tilted about a transverse axis to effect Trendelenburg tilting between a head high position and a head low position. The apparatus of U.S. Pat. No. 5,048,071 also provides for tilting of the patient support table top about a longitudinally extending axis. It is necessary to provide a stationary base anchored to the floor in the foregoing devices because the patient is supported in a cantilevered fashion and is not directly above the base. The footprint of the table top in the above references lies outside the base.

The foregoing structures suffer significant disadvantages. First, medical personnel do not have 360° access to the patient around the entire perimeter of the table top. The side arm that supports the table top is in the way. Second, the stationary base requires a dedicated imaging room with a dedicated floor area for the base. Flexibility is lacking. Third, it is not possible to use a table top having uniform radiolucency. Greater strength is required in the region where the table top is supported, and greater strength is achieved only at the expense of radiolucency. Greater radiation intensity (KV), sufficient to cause penetration in the less radiolucent portions of the table top, is required.

Medical imaging tables having structures as described above have been preferred for various reasons. U.S. Pat. No. 4,541,108 states that a mobile x-ray cannot be tilted, but rather requires that the patient be supported only in a horizontal position. Consequently, a stationery base is deemed necessary. U.S. Pat. No. 5,048,071 refers to devices in which an imaging table is supported either translatively or fixably above a base column, but warns that such arrangements pose problems because supporting tubes, hoses and monitoring lines may become tangled, kinked or pulled loose from a patient, or because access by members of the medical team or radiological examination of any desired portion of the patient's body may be obstructed. Consequently, the table top for supporting the patient is supported off to the side, which requires a stationary base for stability.

Another deficiency of the foregoing devices is that they offer only a single table top. As result, those devices offer no versatility, since no single table top dimensions or configurations are preferred for all diagnostic imaging procedures.

A mobile imaging table comprising a base, a column, and a vertically liftable and longitudinally tiltable table fixedly mounted on a support plate or pedestal directly above the base is available from Beta Medical Products, Inc. of Akron, Ohio (the assignee of the present invention). This imaging table, Model S4008, is described in a brochure captioned "Beta 90/50 Mobile Imaging Table EP Configuration - Model S4008". The support plate and table top mounted thereon can rotate about a transverse axis from +85° (85° in one direction from the horizontal, e.g., head high) to −30° (30° in the other direction from the horizontal, e.g., head low). This imaging table has a single table top. This apparatus can support a weight (i.e., a patient) up to 400 pounds.

An imaging table which includes interchangeable table tops has been advertised and offered for sale under the name of "FasTABLE" in the United States and elsewhere by Diasonics, Inc, (international) of Milpas, California and by OEC-Diasonics of Salt Lake City, Utah. The table therein shows a stationary base, a column extending upwardly from the base, a table top support mechanism extending laterally from the column, and a series of table tops, including a first table top for radiology applications, a second table top for intraoperative applications, and a third table top for urology and gynecology applications. The table top can be raised and lowered, and it can also be rotated longitudinally (a ±30° Trendelenburg-reverse Trendelenburg rotation) and laterally (±20°). This table suffers from the same disadvantages as the other tables having table tops supported outside the base, which have been discussed above.

SUMMARY OF THE INVENTION

An object of this invention is to provide a tilting imaging table in which the patient is supported directly above the base of the apparatus, and in which the base optionally can be mounted on wheels so that the apparatus is mobile.

This invention according to one aspect provides a mobile imaging table comprising a base; a column extending upwardly from the base and comprising a first column member affixed to the base and a second column member which is vertically reciprocable relative to the first member; a longitudinally tiltable table top support means for supporting a removable table top in a position such that at least a portion of the table top is directly above the base, wherein the table top support means is supported by the second column member and reciprocable therewith and is pivotally mounted on a transverse axis which is directly above the base; a removable table top which is adapted to be detachably secured to the support means; and securing means for detachably securing the table top to the support means.

In a preferred embodiment, the base is supported on casters so that the table top is mobile, and the table top support means comprises a pair of spaced vertical corotating pivot arms which are pivotally mounted on a common transverse axis.

This invention according to a second aspect provides a limit stop mechanism for retaining a tilting imaging table in a horizontal position. This mechanism includes a limit stop affixed to a longitudinally tiltable table top support structure, a solenoid operated mechanical stop means movable between a limit stop engaging position and a limit stop disengaging position, and a solenoid which includes a solenoid body, a plunger reciprocable in the body and having one end extending outside the body and connected to the mechanical stop means, and a compression spring inside the body for biasing the plunger and the mechanical stop means to the limit stop engaging position, so that the mechanical stop means engages the limit stop when the solenoid is deenergized and is in a disengaging position when the solenoid is energized. The preferred mechanical stop means comprises a swingable arm which engages the limit stop in one position and is disengaged from the limit stop in another position and a link pivotally connected thereto. This limit stop mechanism can be used with the aforedescribed tilting imaging table and with other tilting imaging tables.

BRIEF DESCRIPTION OF THE DRAWINGS

This invention will now be described in detail with reference to the accompanying drawings, in which:

FIG. 4 is a side elevational view of a pivot arm according to this invention.

FIG. 5 is an end elevational view of the pivot arm shown in FIG. 4.

FIG. 9 is an end elevational view of the table top shown in FIG. 7.

FIG. 10 is an enlarged cross-sectional view of a side strip or "extrusion" on the table top shown in FIG. 7.

FIG. 11 is a side elevational view of a subassembly comprising a pivot arm, a saddle plate and a removable urology table top.

FIG. 12 is a side elevational view of the urology table shown in FIG. 7.

DESCRIPTION OF THE PREFERRED EMBODIMENTS

This invention will now be described in detail with particular reference to FIGS. 1–14, which illustrate the best mode and preferred embodiment thereof.

Figure 1:
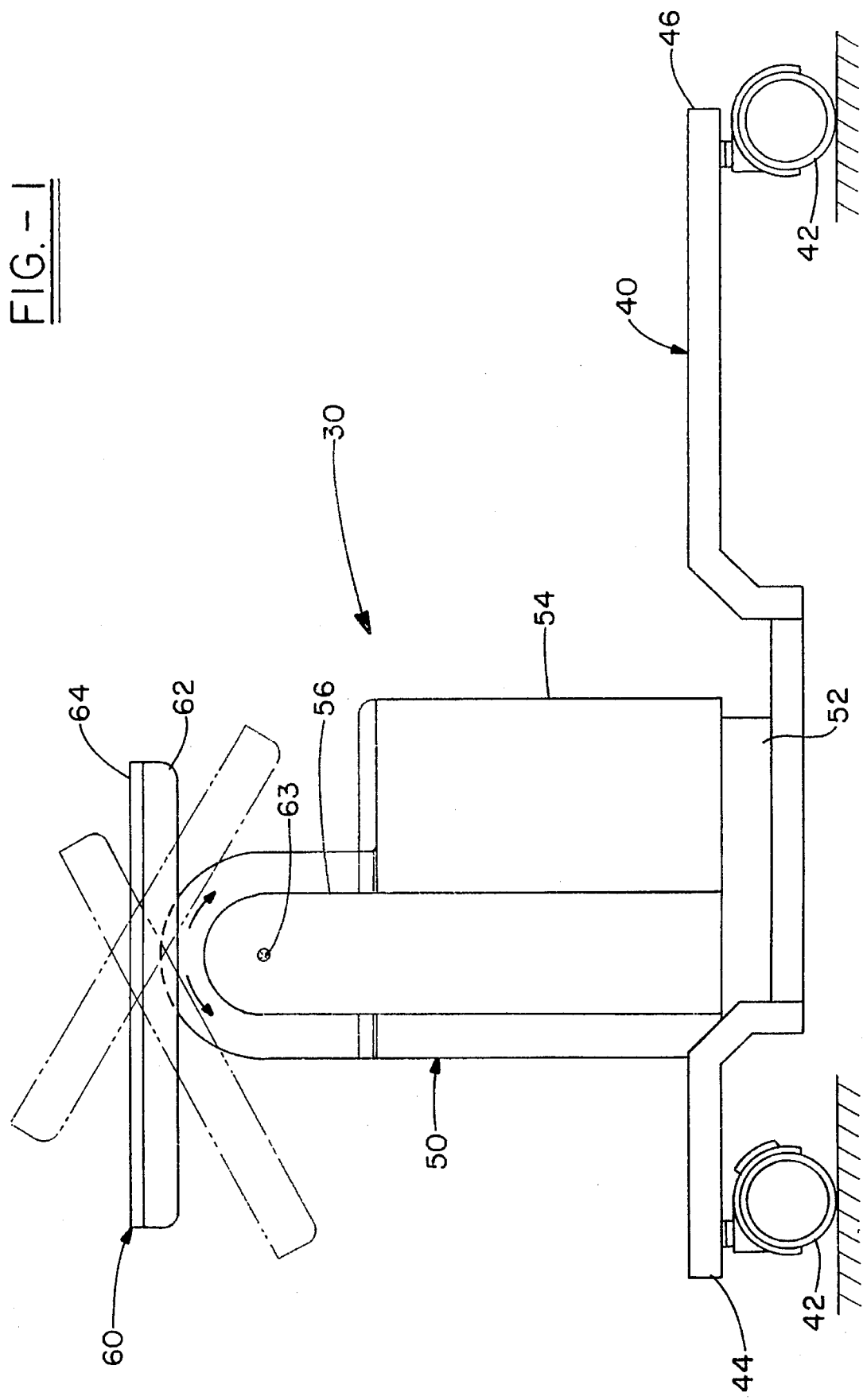
FIG. 1 is a schematic side elevational view of the apparatus of this invention with the table top removed.

FIG. 1 shows the apparatus as a whole according to the present invention. The apparatus of this invention is a tilting table 30 for medical diagnostic and imaging purposes, or more briefly, a tilting imaging table. The table 30 has a longitudinal axis and a transverse axis and comprises a base 40 which is supported on wheels 42, an upright column 50 which comprises a first column member 52 which is affixed to the base 40 and a second upright column member 54 which reciprocates vertically relative to the first column 52, and a tilt assembly 60, which is pivotally mounted on the second column member 54 for rotation about a transverse axis. The tilt assembly 60 comprises a pair of spaced corotating pivot arms 62 (only one of which is shown in FIG. 1), and a saddle plate (or support plate) 64 which is affixed to the pivot arm 62 so that the saddle plate 64 rotates with the pivot arm 62.

Not shown in FIG. 1 is a removable table top. This invention contemplates a set comprising two or more interchangeable and removable table tops for different medical procedures. The preferred table tops are radiolucent so that a patient may be placed thereon for medical imaging procedures such as CT Scan, scintillation imaging, and X-ray. One table top at a time is removably secured to the saddle plate 64 so as to extend longitudinally. The table top chosen is in accordance with the medical procedure to be carried out. For purposes of illustration, this invention will be described in detail with particular reference to a 46 inch radiolucent urology table top for urology examination and imaging procedures, and an 80 inch radiolucent table top for general medical examination and imaging procedures.

The apparatus 30 of this invention affords 360° access to a patient. That is, medical personnel can walk completely around the imaging table 30 and any table top mounted thereon, as is apparent from FIG. 1. Such 360° access is highly conventional. In contrast, an imaging table in which the table top is supported on a side arm (e.g., the tables of U.S. Pat. Nos. 4,541,108 and 5,048,071 cited supra) are less convenient to use, because the side arm forces medical personnel to detour and prevent 360° access.

The preferred base 40 is an open metallic frame of generally rectangular shape and may be mounted on casters 42. (The frame 40 may be mounted on other roller means, such as wheels or rollers, which will permit rolling movement of the apparatus 30 on a floor, but casters are preferred). This frame has a longitudinal direction and a transverse direction, and may be symmetrical with respect to a longitudinal axis. The longitudinal axis of base 40 and of apparatus 30 as a whole are the same. Both the base 40 and the apparatus 30 as a whole have a front end 44 (shown to the left in FIG. 1) and a back end 46 (shown to the right in FIG. 1 ).

The apparatus 30 of this invention is mobile, permitting a patient to be placed thereon at one location, say a patient room of a hospital, and transported to another location, say an examination room or a room which contains imaging equipment such as a CT Scan, a scintillation camera or an X-ray apparatus. By using a radiolucent table top, it is possible to permit the patient to remain on the table 30 of this invention without transfer to another table for imaging purposes. Casters 42, which are placed at each of the four corners of the frame 40, confer mobility to the entire apparatus. Floor locks (not shown) may be provided on the underside of frame 40 to increase stability.

The tilt assembly 60 and with it any table tops removably secured thereto may be tilted longitudinally (i.e., about a transverse axis) from a first or head-high to a second or head-low position. A representative maximum tilt angle of this invention ranges from +30° (30° in one direction from the horizontal, e.g. head-high) (reverse Trendelenburg tilting) to −30° (30° in the other direction from the horizontal, e.g. head-low) (Trendelenburg tilting). A greater maximum tilt angle in one direction, up to 85°, can be provided if desired. A horizontal position is between these two extremes. The tilt assembly 60 and any table top mounted thereon are also vertically reciprocable with the second column member 54 on which the tilt assembly 60 is mounted. The tilt assembly 60 may also be referred as "table top support means".

The upright column members 52 and 54 are preferably housing members of rectangular cross-section, which together enclose an interior space in which mechanical and electrical components for controlling the operation of the present apparatus may be housed. The first or lower housing member 52 is preferably open at both ends, although the lower end may be closed if desired by horizontal plate not shown. The second or upper housing member 54 may have a dome portion 56 in the shape of an inverted "U". The upper end of upper housing member 54 is closed while the lower end is open. Two housing members 52 and 54 are arranged in telescoping relationship. Preferably the lower portion of upper housing member 54 is slightly larger in both length and width than the lower housing member 52.

A lift mechanism for raising and lowering second housing member 54, and with it the tilt assembly 60 and a table top secured thereto, may be housed inside the housing formed by member 52 and 54. An electromechanical lift mechanism is preferred. Such mechanism may include, for example, a motor driven screw jack, guide rails to guide the vertical reciprocating movement of the second housing member 54, and a pair of limit switches for limiting the extent of vertical travel. Lift mechanisms for raising and lowering a table for medical purposes known in the art, and may be used in the present invention. Details of a lift mechanism do not form a part of this invention.

Figure 2:
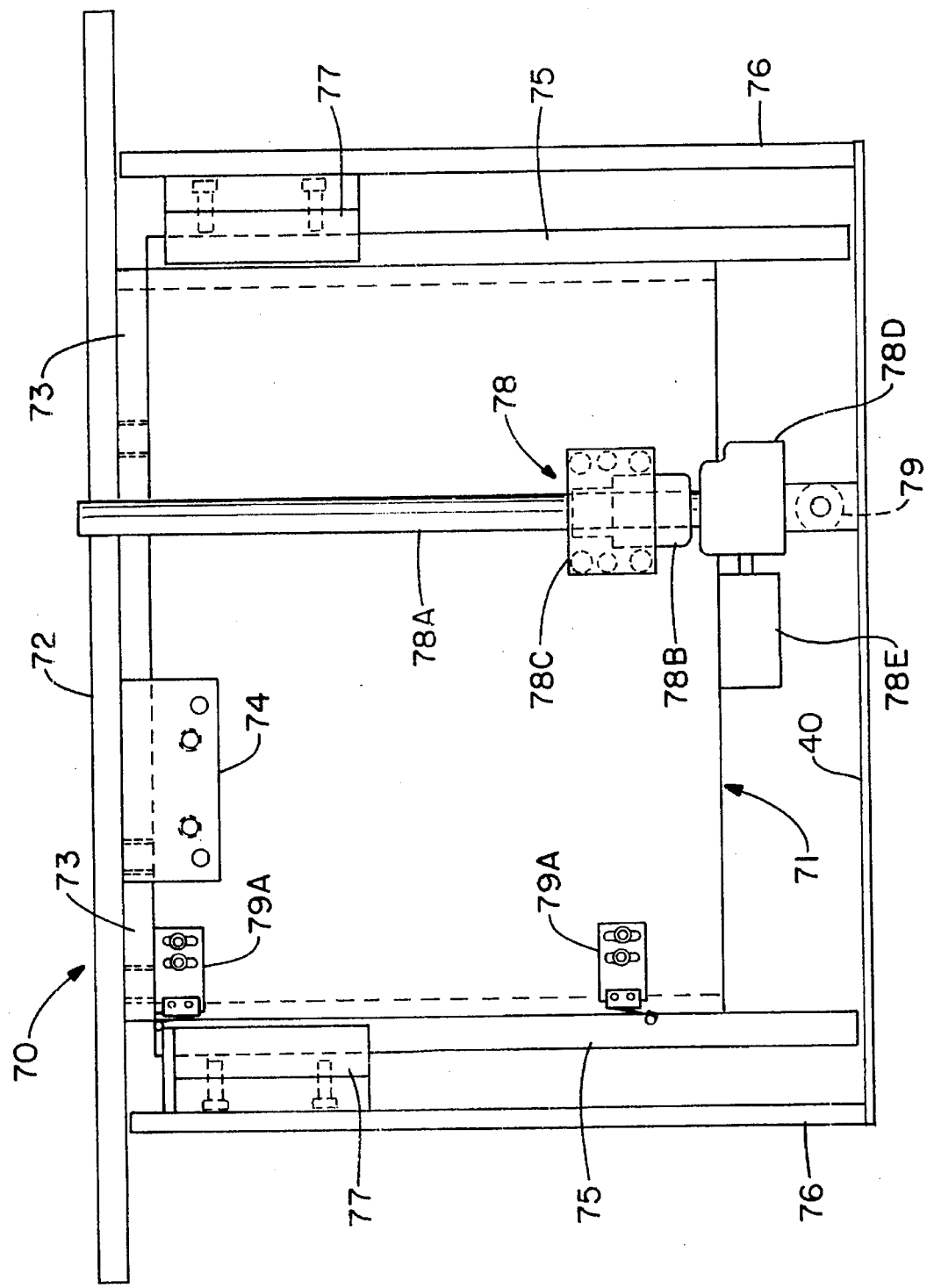
FIG. 2 is a from elevational view of a lift mechanism according to this invention.

FIG. 2 shows a preferred lifting mechanism 70 for the apparatus 30 of this invention. Lifting mechanism 70 includes a vertically reciprocable tubular carriage assembly 71. Carriage assembly 71 comprises a pair of spaced vertical face plates and a pair of spaced vertical side plates which are welded together to form an open ended tubular enclosure of rectangular cross-sectioned shape. Carriage assembly 71 further comprises a pair of horizontal rectangular blocks 73 which are welded to the tubular plate assembly enclosure at the top end thereof. This entire carriage assembly 71 is bolted to a horizontal tilt plate 72. Tilt plate 72 is affixed to upper housing member 54. Also bolted to the tilt plate 72 for added strength are a pair of carriage support blocks 74. A pair of vertical linear bearing rails 75 are affixed (e.g., by bolting) to the carriage assembly 71. A pair of stationary vertical bearing mounting plates 76 extend upwardly from frame 40. Linear bearings 77 are mounted on mounting plates 76. Spacers (unnumbered) may be interposed between the bearing 77 and the bearing mounting plates 76. These bearings permit reciprocating movement of the carriage assembly and handles the vertical forces and moment load (i.e., the weight of a patient on a table top) of the apparatus. A preferred bearing is HRW-35, made by THK of Japan. A linear activator assembly 78 comprising a ball screw 78A, a ball nut 78B and a ball nut block 78C welded to the vertical tubular carriage assembly 71. The lower end of ball screw 78A is received in right angle drive 78D. A drive motor 78E drives the carriage assembly 71. The linear activator assembly 78 is fastened to frame 40 by means of a clevis pin 79. Limit switches 79A limit vertical movement of the carriage assembly 71. The amplitude of carriage assembly movement may be as described; an amplitude of 10 inches is normally preferred. A tilt enable switch, not shown, may be provided to prevent tilting of the tilt assembly 60 until carriage assembly 71 is in its raised position.

Figure 3:
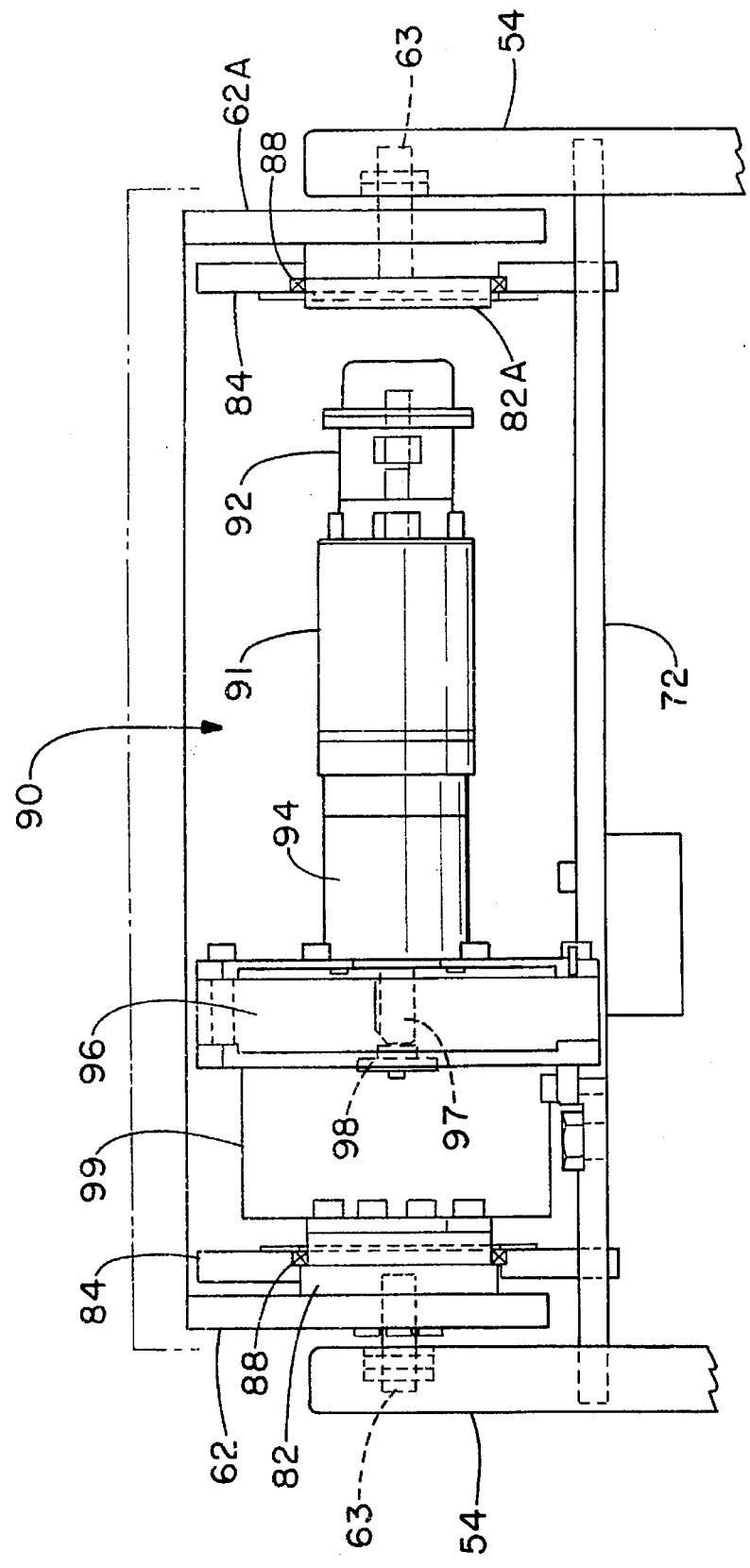
FIG. 3 is an end elevational view of a tilt assembly according to this invention.

Referring now to FIG. 3, tilt assembly 60 comprises a pair of spaced vertical plate-like pivot arms 62 and 62A. The pivot arms are rotatable mounted on respective pivot shafts 63, which are coaxial. Drive side pivot arm 62 is fixedly secured (e.g., with dowels) to a drive side shaft 82, which receives a pivot shaft 63. Similarly, idler side pivot arm 62A is fixedly secured to an idler side shaft 82A, which receives a pivot shaft 63.

It will be noted that the shafts 82, 82A and the pivot shafts 63 are coaxial. Drive side shaft 82 and idler side shaft 82A are rotatably supported by respective bearing plates 84 which in turn are supported on tilt plate 72, which also serves as a drive mounting plate. Bearings 88 are interposed between the respective bearing plates 84 and the respective drive shaft so as to permit rotation of the drive shaft.

FIG. 3 also illustrates a preferred tilt drive mechanism for rotating the pivot arm 62, saddle plate 64 and a table top secured thereto. The tilt drive mechanism 90 is supported on horizontal tilt plate (or drive mounting plate 72), which extends from one side to the other of the upright column housing 50 and is fixedly secured to the upper housing member 54. Drive mechanism 90 comprises a PM field servo motor 91, a brake 92, and a gear reducer 94, all of which are coaxial with the pivot shafts 63 of pivot arms 62 and 62A. The drive mechanism further comprises a harmonic wave generator 96, a drive shaft 97, and a cap wave generator 98 and a harmonic drive 99, all of which are also coaxial with the pivot shafts 63. An 8M harmonic drive is preferred although a 4M harmonic drive can be used. The harmonic drive output is secured to and drives a drive side shaft 82, which in turn drives pivot arms 62 through its pivot shaft 63. Limit switches (not shown) may be provided to limit the extent of tilting in each direction.

It will be noted that only one of the two pivot arms, i.e. the pivot arm 62 shown to the left in FIG. 3, is driven.

The imaging table 30 of this invention is capable of supporting a load (e.g., a patient) of 400 pounds. The tilt drive mechanism shown in FIG. 3 is primarily responsible for this ability to support a heavy load.

Other tilt drive mechanisms for longitudinally tilting a medical examination table are known in the art and may be used in place of the preferred mechanism shown, if desired.

A pivot arm 62 is shown in detail in FIGS. 4 and 5. The other pivot arm 62A, which is not shown in FIG. 4 or FIG. 5, is a mirror image of pivot arm 62; the two pivot arms are therefore structurally similar.

As shown in FIGS. 4 and 5, each pivot arm 62 (and 62A) has a horizontal longitudinally extending upper portion 100 for supporting a support saddle plate 64 (shown in FIG. 1), and a U-shaped portion 101 extending downwardly therefrom and longitudinally. A hinge pin 102 extends inwardly from the upper portion 100 of pivot arm 62 near the forward end thereof. The respective hinge pins 102 of the respective pivot arms 62, 62A are coaxial. The hinge pins 102 are used in removably securing a table top to the tilt assembly 60 as will be described subsequently. Each pivot arm also has a plurality of sets of bolt holes 103, 104, 105 and 106 (4 sets are shown) having vertical axis and extending through the upper portion 100 of pivot arm 62, for attachment of a saddle plate.

Figure 6:
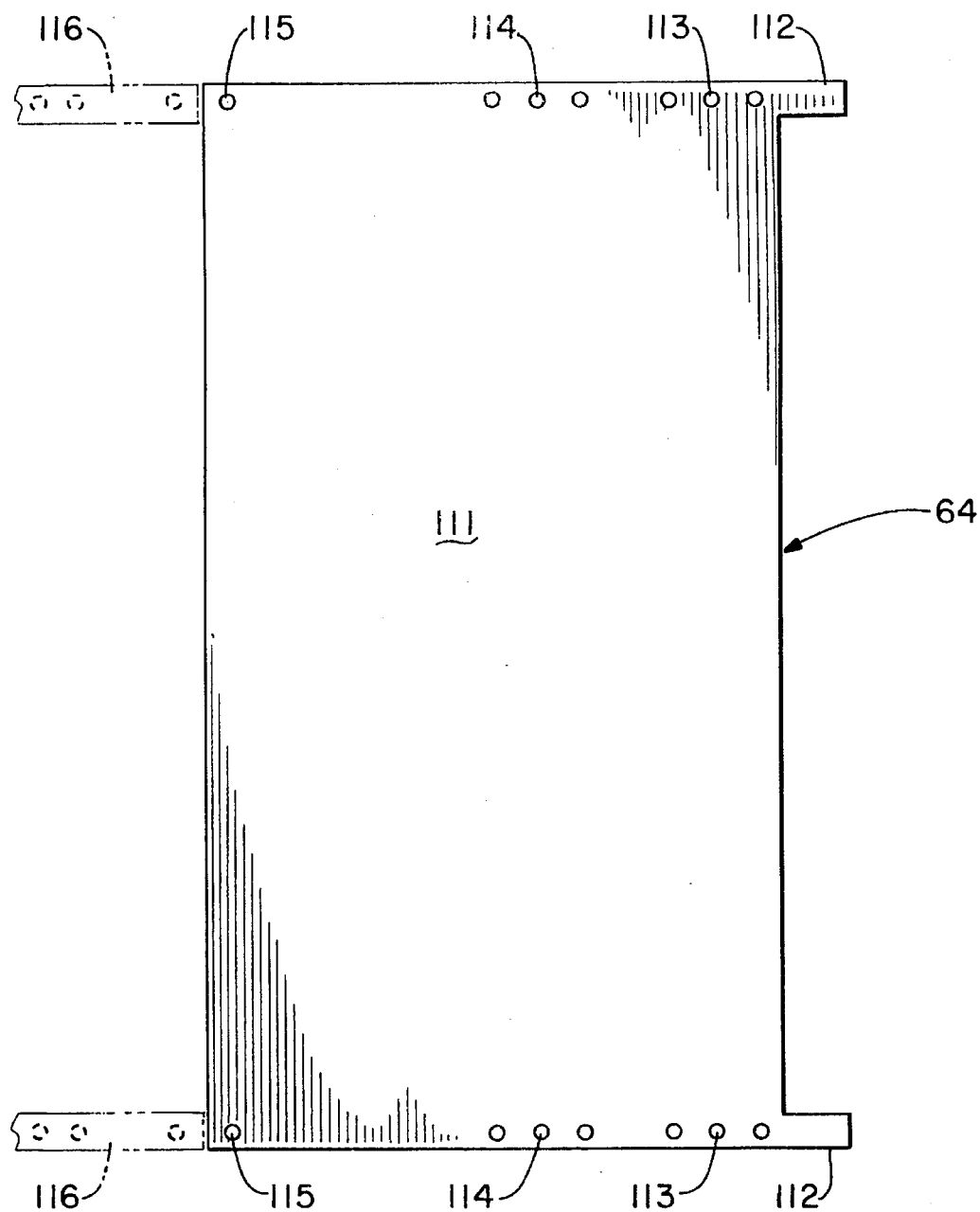
FIG. 6 is a top plan view of a table top support plate, or saddle plate, for the apparatus of this invention.

FIG. 6 shows in plan view a support saddle plate 64 which is affixed to the pivot arms 62 by bolting, as will be described. Saddle plate 64 together with the pivot arms 62 and 62A form tilt assembly 60, which is a mounting or support structure for supporting a removable table top. Saddle plate 64 is of generally rectangular shape, comprising a rectangular main portion 111 and a pair of forwardly extending strips or ears 112, which are located along the two lateral edges of saddle plate 64. The rectangular main portion 111 and the forwardly extending ears 112 together form a void or cut-out portion, at the forward end of saddle plate 64, for a pair of hinge blocks (to be described subsequently) for removably securing a table top to a pivot arm 62 (or 62A) via hinge pins 102.

Saddle plate 64 may be permanently affixed to pivot arms 62 and 62A. Both are components of tilt assembly 60. This end, the saddle plate 64 has two rows of vertical bolt holes which are adjacent to the respective lateral edges of the saddle plate 64. Each row of bolt holes includes a first set 113 and a second set 114, which are lined with set 103 and 104, respectively, on the pivot arm 62, and a single bolt hole 115, near the rearward end of the saddle plate 64, which is aligned with one of the bolt holes in set 105, when the saddle plate 64 is in place and properly aligned on top of the pivot arms 62.

A tilt assembly 60 further includes a pair of rectangular spacers 116, which are shown in phantom lines in FIG. 6. They are also shown in FIGS. 11 and 12. These spaces 116 are of the same thickness as saddle plate 64 and extend from the rearward edges of the saddle plate 64 on top of the pivot arm 62. These spaces 116 have vertical bolt holes for affixation to the pivot arm 62.

The pivot arms 62 and 62A, saddle plate 64, and spacers 116 together form tilt assembly 60, which is adapted to support a removable table top for tilting movement. The tilt assembly 60 may rotate through a desired arc. A preferred tilt assembly according to this invention rotates between a 30° head up position and a 30° head down position. Between these two limits of travel is a horizontal position as shown in solid lines in FIG. 1, in which the support arm 100 of pivot arm 62, and the saddle plate 64 mounted thereon and secured thereto are in a horizontal position.

Figure 7:
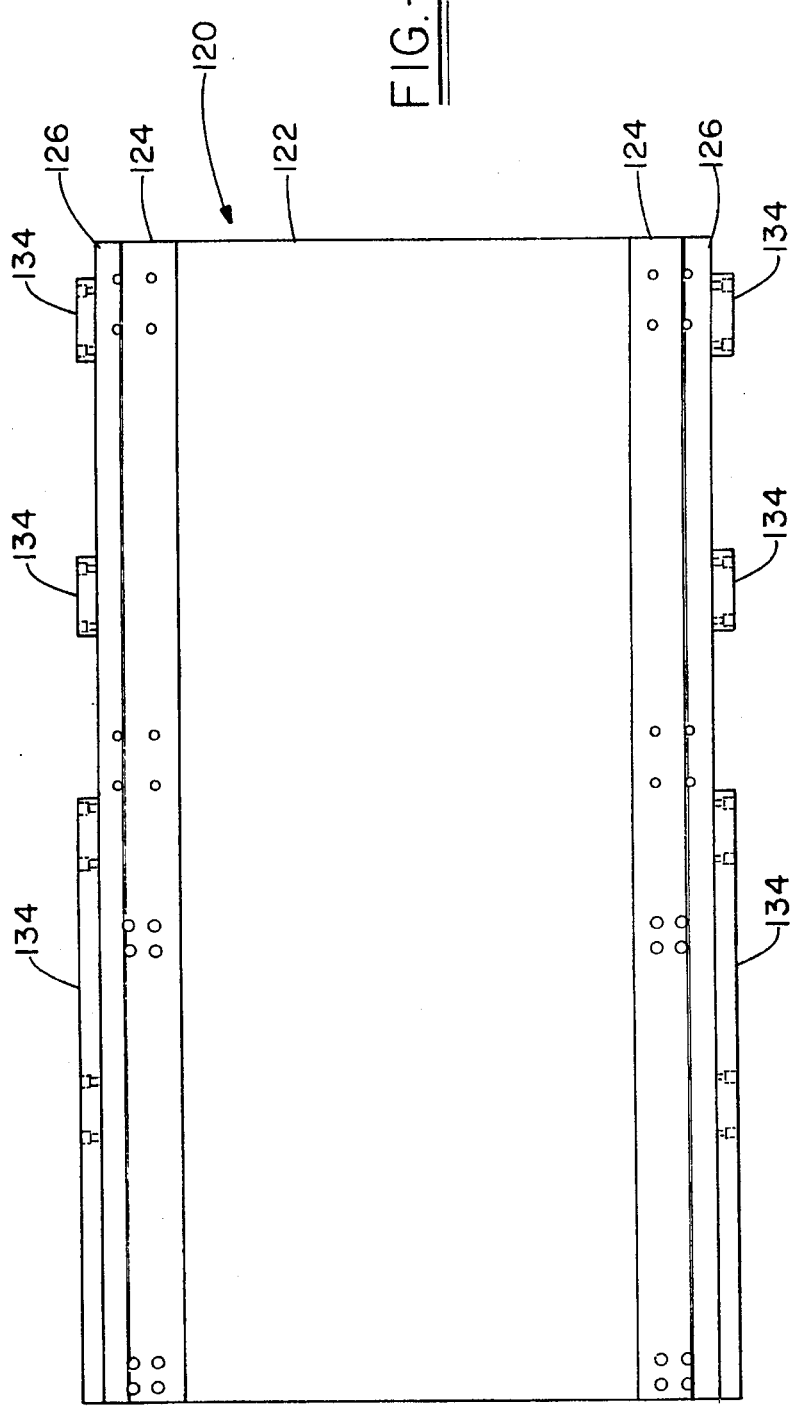
FIG. 7 is a plan view of a detachable table top suitable for urology examination and imaging.
Figure 8:
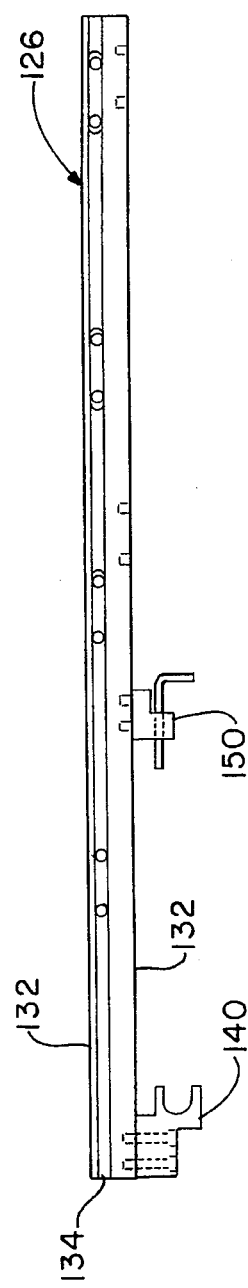
FIG. 8 is a side elevational view of the table top shown in FIG. 7.

FIGS. 7, 8 and 9 are a top plan view, a side view, and an end-view, respectively, of a urology table 120, which is a preferred table top according to the present invention. Urology table top 120 is intended for use in urology examination and imaging procedures. The preferred urology table top 120 is 46 inches long, which is long enough to support most adult males from the head to the knees, while permitting the lower portions of a patient's legs (below the knees) to dangle downwardly beyond one end of the urology table top. Normally, for urological examination and imaging the patient will be placed on the urology table top so that the patient's head is above the front end of the frame 40.

The urology table top 120 comprises a rectangular and longitudinally extending radiolucent main portion 122, a pair of longitudinal rectangular side strips 124, and a pair of generally U-shaped longitudinally extending extruded metal members (or extrusions) 126, all of which are bonded together to form an integral unitary structure.

The radiolucent portion 122 is preferably made of a radiolucent carbon fiber composite. Such material is well known in the art as a radiolucent material for table top use for medical imaging procedures. The radiolucent main portion 122 is preferably slightly arcuate in shape, being slightly lower along longitudinal center line than along the side edges which the side strips 124. Metallic side strips 124 are preferably aluminum. The extrusions 126 are also preferably aluminum.

The radiolucent portion 122 of table top 120 is preferably of uniform radiolucency. The radiolucent portion 122 may be highly radiolucent, permitting the imaging apparatus (e.g., CT Scan or x-ray) to use a low level of radiation.

Each extrusion 126 comprises a horizontal upper portion 128, horizontal lower portion 130 which is spaced from the upper portion 128, a vertical side portion or connecting portion 132 which connects the upper and lower portions, and a horizontal side extension 134 which extend horizontally outwardly from the vertical portion 132. The vertical portion 132 may have two spaced sets of bolt holes to receive a hinge block and a locking block, respectively, as will be described subsequently with reference to FIGS. 11 and 12. The side extension 134 may have a plurality of spaced horizontal bolt holes for attachment of accessories (not shown). Urology table top 120 further comprises means for removably securing the urology table top to the tilting assembly 60. The preferred means, shown in FIGS. 11 and 12, comprise a hinge block and a locking block.

Referring now to FIGS. 11 and 12, a urology table top 120 has two hinge blocks 140, which are permanently attached both at the two forward corners of the table top 120. Each hinge block 140 comprises a block portion 142 having a plurality of vertical bolt holes 144 therein (a 2-x-2 arrangement is preferred), and a generally channel-shaped or U-shaped hinge pin receiving portion or receptacle 146, which extends rearwardly from the block portion 142, for receiving a hinge pin 102, which has been previously described with particular reference to FIGS. 4 and 5. It will be observed that the "U" of the U-shaped receptacle 146 is turned sideways so that the arms of the U (and consequently the open portion between the two arms) face rearwardly. The bolt holes 144 in hinge block 140 are adapted to be aligned with bolt holes (unnumbered) of the extrusion 126 of table top 120.

Also attached by bolt to the underside of table top 120, and specifically to the extrusions 126 along the lateral edges thereof, are a pair of locking blocks 150, one on either side of the table top. Each locking block has a horizontal bore 151 which receives plunger assembly 152 which comprises a spring pressed, L-shaped locking plunger 154 which reciprocates within a cylindrical body 156. Plunger 154 is generally L-shaped and has a downwardly extending handle 158. The plunger assembly is a commercially available item.

FIG. 11 is a schematic side view showing a pivot arm 62, support saddle plate 64 and table top 120. As shown in FIG. 11, each hinge block 140 mounted on an extrusion 126 on the underside of table top 120 near the forward edge of the table top 120. Also as shown in FIG. 11, a pair of locking blocks 150 are mounted on respective extrusions 126 on the underside of table top 120, just behind the depending U-shaped portion 101 of the pivot arm 62 (or 62A, not shown in FIG. 10). The hinge blocks are mounted on the extruded metal side members 126. The hinge blocks 140 and the locking blocks 150 are located laterally slightly inboard of the pivot arm 62 and spacers 116, as may be best appreciated in FIG. 6.

FIG. 12 is a schematic side view of a table top 120 according to this invention, with hinge block 140 and a locking block 150 shown thereon but with other details (shown in FIGS. 7 and 8) omitted.

As shown in FIG. 12, a table top 120 is releasably secured to a saddle plate 64. The receptacles 146 of the two hinge blocks 140 engage the underside of the saddle plate 64 at the forward edge of the saddle plate, and the plungers 154 of the two locking blocks 150, when their extended position shown in FIG. 12, engage the underside of saddle plate 64 near the rearward edge thereof. To release a table top 120, it is merely necessary to pull the plunger 154 to its retracted position, using handle portion 158 thereof, and then to lift the table top 120. To lift the table top 120, one first lifts the table top near the hinge block 150, while pivoting it upwardly, using the pivot pins 102 as a fulcrum, then moving the forward edge of the table top slightly away from the hinge pins 102 so as to disengage the table top from the pivot arms.

Figure 13:
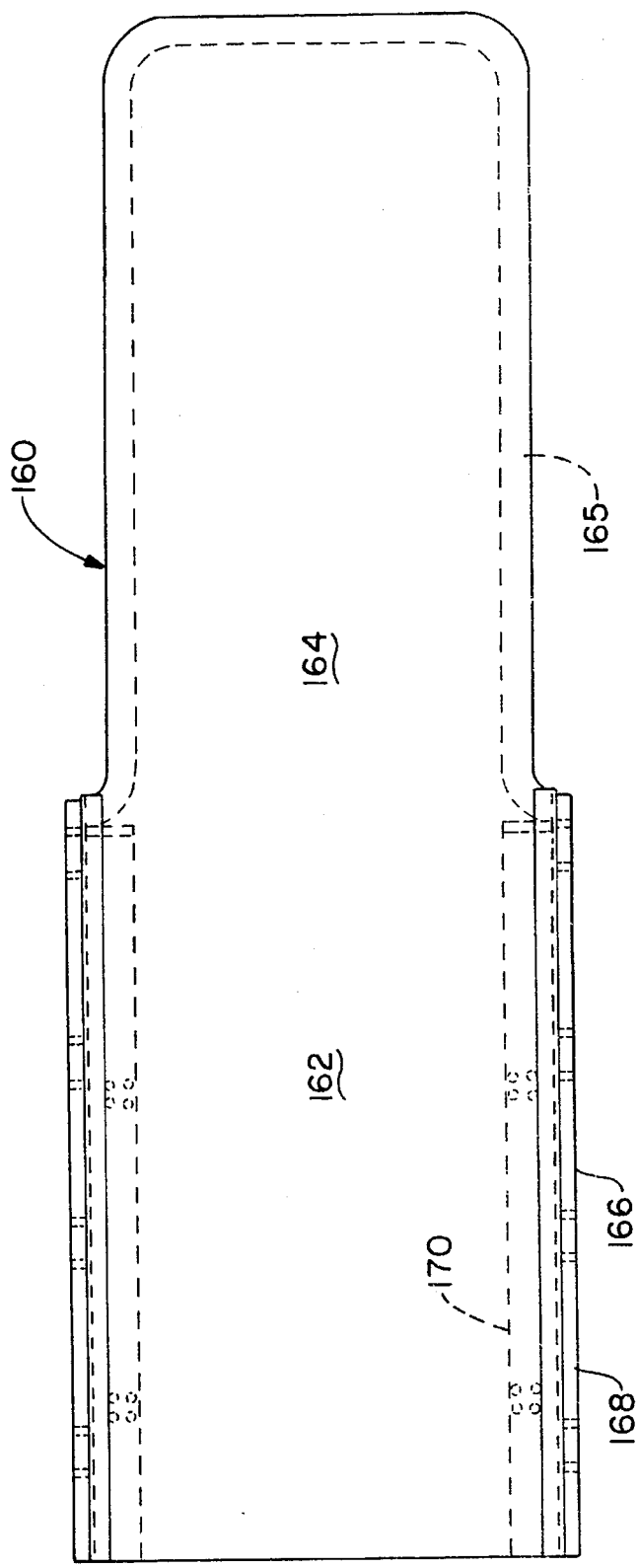
FIG. 13 is a plan view of an 80 inch table top suitable for general examination and imaging procedures.
Figure 14:
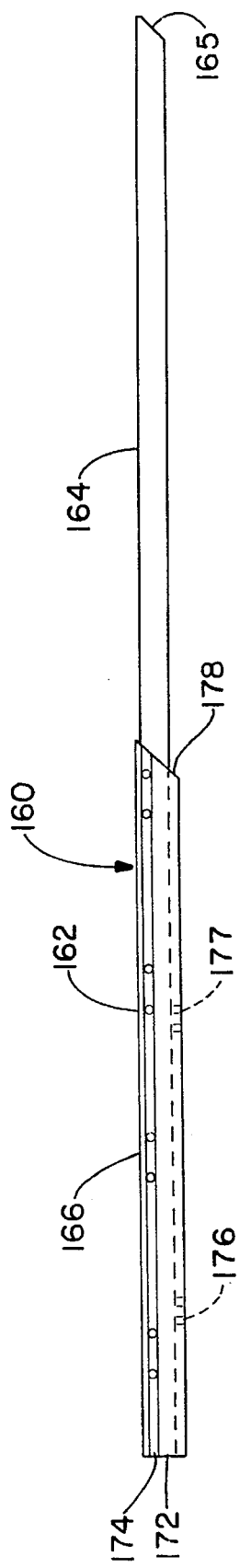
FIG. 14 is a side elevational view, with attaching members for securing the table top to a saddle plate omitted, of the general examination table top shown in FIG. 13.

FIGS. 13 and 14 show a second table top 160 for medical procedures. Second table top 160 is a table top for general imaging procedures. At end of table top 160 is shown to the left in FIGS. 13 and 14.

Table top 160 is of sufficient length so that a patient may lie down in outstretched position thereon, with the entire length of the body from head to feet supported on the table top. A length of 80 inches is sufficient to fully support most patients in an outstretched position and is preferred.

Table top 160 is made of a radiolucent material such as carbon fiber. Table top 160 comprises a head portion 162 and a foot portion 164. The head portion 162 is preferably slightly wider than a saddle plate 64 on which it is adapted to be supported. The head portion 162 has vertical edges, i.e., a vertical head edge and parallel vertical side edges. Foot portion 164 is slightly narrower than the head portion, and has beveled edges along its sides and back. A bevel angle of 45° is preferred. The beveled edges face downwardly, so that the overall width of the foot portion, measured on the underside is slightly less than the overall width measured on the top side. Similarly, the overall length of the table top 160 measured on the underside as slightly less than the overall length measured on the top side.

A pair of longitudinally extending extruded metal members or simply extrusions 166 surround and protect the side edges of the head portion 162 of table top 160. These extruded metal members are structurally similar to their counterpart 126 shown in Fig. 10. Thus, the extruded metal members 166 each comprise a horizontal or upper portion 168, a horizontal bottom portion 170 which is spaced from the top portion 168 so that a side edge of the table top 160 may be received therebetween, a vertical portion 172 which connects the upper and lower portions 168 and 170, and horizontal side extension 174 which projects outwardly from the vertical portion 172. Side extension 174 has the bolt holes, similar to those shown in FIG. 10, to permit attachment of accessories.

The bottom portion 170 of each of the extruded metal members 166 has a first set of bolt holes 176 near the head end for attachment of a hinge block 140, which has been previously described. The bottom portion 170 of each extruded metal member 166 also has a second set of bolt holes 177 for attachment of a hinge block 150. An important feature of the present invention is that all table tops supplied to the apparatus of this invention are removable and interchangeable. That ends, the configuration of bolt hole sets 166 and 167, and the distance between these two sets of bolt holes, are exactly the same as is the case with the corresponding sets of bolt holes which are present in a urology table top 120, as shown in FIG. 7.

The only structural difference between the extruded metal members 166 for a general examination table top 160, and the extruded metal members 126 for a urology table top 120, is that the extruded metal members 166 extend longitudinally only along the side edges of the portion 162 of table top 160, and end where the head portion 162 meets the foot portion 164 of table top 160 near the longitudinal center of table top 160.

The extruded metal members 166 extend only over the head portion 162 of the table top 160, so that the foot portion 164 will be free of any radiopaque material. This is important in providing maximum suitability for imaging. It should also be noted that a patient will usually lie on the table top 160 so that his/her head and upper body are supported on the foot portion of the table top, and the feet and legs are supported on the head portion.

It will be further noted, from the position of bolt holes 176, that a general examination table top 160 is secured to a tilt assembly 60, (and specifically to a support saddle plate 64 thereof), so that there is appreciable overhang (about 12 inches to 18 inches typically) of the table top 160 beyond what is supported on the saddle plate 64. This is done for stability, so that the patient's center of gravity will lie directly above the base 40 of the apparatus.

An apparatus according to this invention may be provided with additional table tops other than the urology table top 120 and the general examination and imaging table top 160 which have been specifically illustrated. All of the table tops in a set will utilize identical hinge blocks 140 and locking blocks 150, and will have the same configuration of bolt holes for attachment of the hinge and the locking blocks, so that all table tops in a set are interchangeable. A purchaser may acquire as many table tops as are desired at the time of initial purchase of the apparatus, and can then acquire additional table tops later. Also, extensions for the table tops 120 and 160 may be provided.

To assemble the table top of this invention, one first selects one of the removable table tops, depending upon the medical examination/imaging procedure desired. By way of a first example, suppose a urological imaging procedure is to be carried out. One places a urology table top 120 in position on the support saddle plate 64 by hinge blocks 140 at the head end of the table top into engagement with the hinge pins 102 of the respective pivot arms 62 and 62A. The remainder of the table top is still slightly raised. Then the remainder of the table top is lowered to a horizontal position until the table top engages the entire length of a saddle plate 64, with the hinge blocks plungers 154 retracted. The plungers are then moved to their extended or locking position. The apparatus is now ready to receive a patient.

A patient climbs on to the table top with his/her head at the head end of the table. The table top can be raised, and the patient's head can either be raised or lowered via the tilting mechanism as needed. After examination and/or imaging are complete, the table top is returned to horizontal position if it has been tilted, and is lowered to the lower most position if it has been raised.

By way of a second example, suppose that an examination and/or imaging procedure which requires the patient to be in an outstretched position is to be carried out. Then the long table top 160 is secured to the table top mounting assembly in the manner described above. Then, with the table top horizontal and in its lower most position, the patient climbs onto the table top with the head of the patient at the foot of the table top and conversely the feet of the patient at the head end of the table top. This can be done either in an examination or imaging room, or a hospital patient room. Since the preferred apparatus is mobile, a patient can be transferred from a hospital bed to the table top 160, and the table then wheeled through hospital corridors to a medical examination or imaging room. Then the table top can be raised and/or tilted as desired. Then, after examination and/or imaging are complete, the table top is returned to a horizontal position and is lowered to its lowermost position. The patient can then be returned to his/her room.

A table according to the present invention offers several advantages over tables for medical examination and/or imaging procedures currently in use. First of all, the table according to this invention offers a set of interchangeable table tops, so that one can select the table top most appropriate for a given procedure. This confers great versatility.

Secondly, a table according to the present invention is very stable and supports a patient in a very stable manner. At least a portion of the table top support structure 60, and preferably the entire structure 60 is directly over base 40. Then, when a table top (120 or 160, for example) is affixed, at least a portion of the table top, and at least a portion of the patient's body are directly above the base 40. In fact, the apparatus of this invention is so arranged that both the center of gravity of the patient and the center of gravity of the entire system (table plus patient) will be directly above the base 40. This leads to at least two desired consequences. First, the patient is positioned in a very stable manner. The positioning is precise enough so that, if imaging of the same part of a patient's body is required on more than one occasion separate images can be taken from precisely the same image point so that the image is taken on successive occasions can be readily compared. Another desired consequence of placing the patient directly above the base of the apparatus is the apparatus can be made mobile. This is not possible in an apparatus in which a patient is supported when the generally arm that extends out beyond the base of the apparatus.

Third, the apparatus of this invention is mobile. This confers increased flexibility and improved space utilization. A hospital imaging room does not require a dedicated floor area for a base for the imaging table. The imaging table can be wheeled from place to place and positioned as needed. In fact, the imaging apparatus can be made portable and wheeled from place to place if desired, so that a dedicated imaging room is not necessary. Other advantages have been discussed earlier.

It is believed that the apparatus of the present invention is the first for medical imaging procedures which provides interchangeable table tops in a structure in which a patient is supported directly overhead, so that at least a part of the patient's body is directly over the base of the apparatus. It is also believed that the apparatus of the present invention is the first to provide a mobile examination and imaging table having interchangeable table tops.

LIMIT STOP TO PREVENT TILTING

Figure 16:
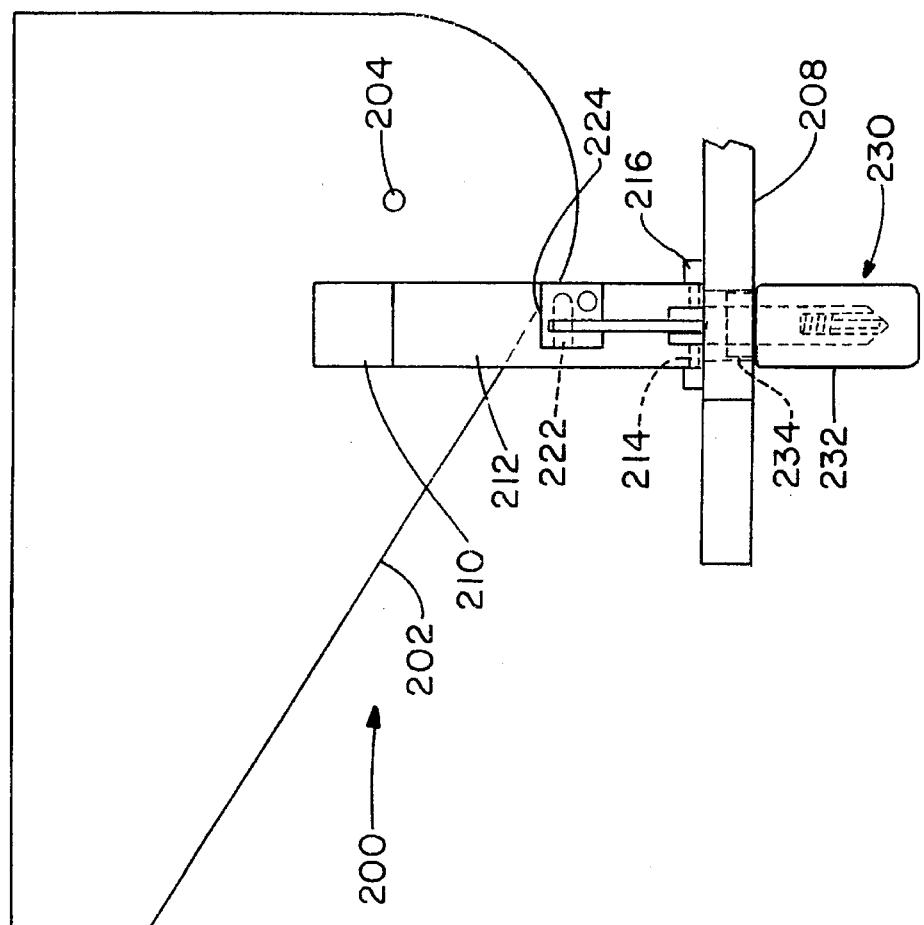
FIG. 16 is a side elevational view of the apparatus shown in FIG. 15.
Figure 15:
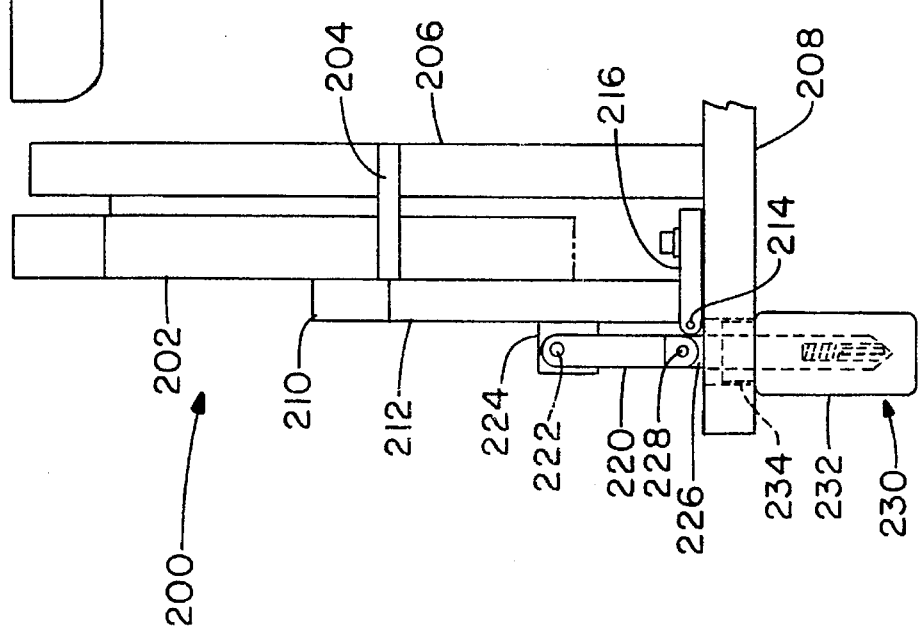
FIG. 15 is an end elevational view of a limit stop mechanism for a tilt mechanism of a tilting imaging table.
Figure 17:
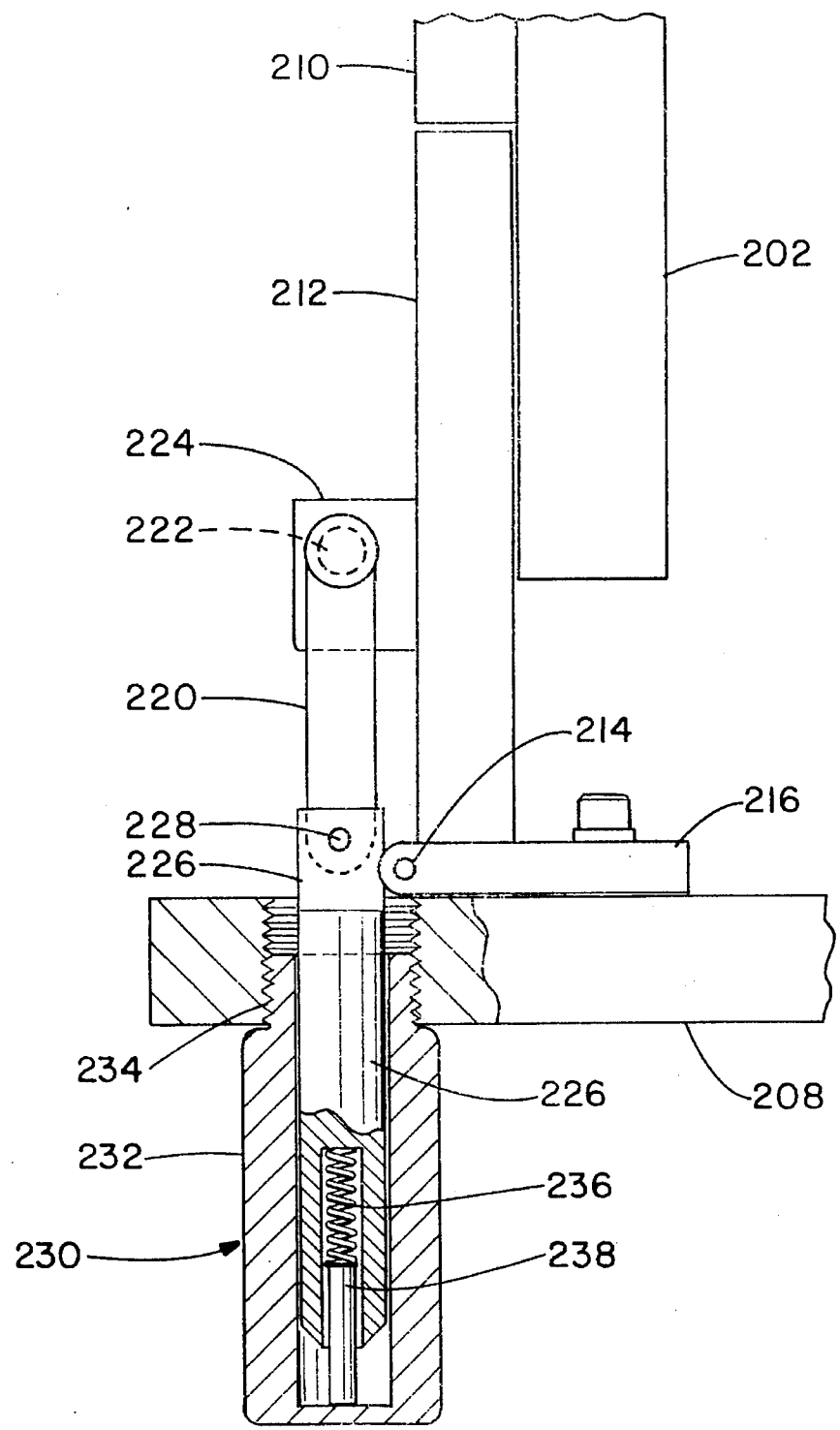
FIG. 17 is an enlarged end elevational view, with parts broken away and parts shown in section, of a portion of the apparatus shown in FIG. 15.

A limit stop mechanism for preventing rotation of a tilt assembly of a tilting imaging table is shown in FIGS. 15, 16 and 17. The limit stop mechanism to be described with reference to FIGS. 15–17 can be used with the tilting table described with reference FIGS. 1–14 and with other longitudinally tiltable tables used for medical procedures such as medical examination and imaging.

Referring now to FIGS. 14 and 15, apparatus 200 indicates generally an apparatus which includes a tilting mechanism for a medical examination and imaging table, and a limit stop mechanism for preventing rotation of the tilting mechanism.

Apparatus 200 comprises a table top support structure which includes a pair of rotatable pivot arms 202, only one of which is shown. Pivot arm 202 is rotatable mounted on a pivot shaft 204, which rotates about a fixed horizontal axis. Pivot shafts 204 of the two pivot arms are coaxial. Each pivot shaft 204 may be rotatably mounted to a suitable vertical mounting plate 206, which in turn is supported on a horizontal mounting plate 208.

The two pivot arms 202 support an examination and imaging table top (not shown). Table top may be either fixably secured or removable secured to a tilting assembly which includes the pivot arms 202. Tilting assembly may include a support saddle plate similar to plate 64, shown in FIGS. 1–14, to which a table top may be removably secured as described with reference to FIGS. 1–14. Alternatively, a table top may be fixably secured to a tilting assembly by means known in the art.

A table top assembly which includes pivot arms 202 may rotate through any desired arc. For example, longitudinally tiltable table top assemblies capable of rotating from +30° (head up) to −30° (head down) are known and other table top assemblies capable of rotating from +85° (head up) to −30° (head down) are also known, and the limit stop mechanism of FIGS. 15–17 can be applied to either of these, as well as to other longitudinally tiltable tables for medical examination and imaging purposes. A tilt mechanism is illustrated herein as having a pair of pivot arms 202, but the limit stop means of FIG. 15–17 can be applied to other tilt mechanisms capable of producing longitudinal tilting of an examination and imaging table.

The limit stop 210 is affixed to pivot arm 202 so as to rotate therewith. Limit stop 210 has a planar lower surface which forms an abutment surface. Coacting with the limit stop 210 is a mechanical stop assembly, which includes a swingable arm 212 and a link 220. Swingable arm 212 is swingable about a horizontal axis at its lower end between the limit stop engaging position, shown as solid lines in FIG. 15, and a limit stop disengaging position, shown in dotted lines in FIG. 15, with all except the upper end of the swinging arm broken away. Swingable arm 212 is rotatably mourned on roll pin 214, which is received in a stationary mounting bracket 216 affixed to mounting plate 208. Rotation of the swinging arm 212 is accomplished by means of solenoid operated mechanical link 220. Link 220 has at its upper end a hole which receives a pin 222, which in turn is received in a connecting bracket 224 that is affixed to the swinging arm 212.

Link 220 is pivotally connected at its lower end to a plunger 226 by means of a pin 228 (best seen in FIG. 17). Plunger 226 is basically cylindrical but has a flattened upper end to receive the lower end of link 220.

Referring now to FIG. 17, plunger 226 is vertically reciprocable and is controlled by solenoid 230. Solenoid 230 has a generally cylindrical upright body 232, which may be received in horizontal mounting plate 208 by means of a screw threaded socket 234. A body 232 has a central bore in which plunger 226 reciprocates. The lower end of plunger 226 has a bore which receives a compression spring 236 and a dowel pin 238. The upper end of plunger 226 extends outside the solenoid body 232. When the apparatus is not in use, the swinging arm 212 is in the upright position shown in Figs. 15, 16, and 17, and in this position is in abutting relationship with the limit stop 210, so that the pivot arm 202 and consequently the entire tilting assembly and any table top mounted thereon are held in a horizontal position. When the swinging arm 212 is in this upright position, compression spring 236 is in its normal or unstretched position and the lower end of plunger 226 is spaced from the lower end of the bore in body 232.

When it is desired to tilt the tilt assembly and any table top mounted thereon, this solenoid 230 is energized. This draws the plunger 226 down against the bias of compression spring 236. Plunger 226 is drawn downwardly, which in turn causes the mechanical link 220 to be drawn out downwardly, causing the swing arm 212 to swing outwardly away from the pivot arm 200 and limit stop 210 to a limit stop-disengaging position. The tilt assembly including pivot arms 200 can then rotate. The limit stop mechanism shown in FIGS. 14–16 is a highly efficient mechanism for preventing unwanted rotation of a tilt assembly (including pivot arm 202) and any table top which may be mounted thereon.

While this invention has been described in detail with particular to the preferred embodiment thereof, it shall be understood that this description is by way of explanation and not by way of limitation.

What is claimed is:

1. Apparatus for supporting a patient for medical diagnostic imaging purposes, said apparatus comprising:
   (a) a base supported on casters whereby the apparatus is mobile;
   (b) a column extending upwardly from said base, said column comprising a first column member affixed to said base and a second column member which is vertically reciprocable relative to said first member;
   (c) longitudinally tiltable table top support means for supporting a removable table top in a position such that at least a portion of said table top is directly above said base, said table top support means being vertically reciprocable with said second column member and pivotally mounted on a second column member for rotation about transverse axis which passes directly above said base and through said second column member, said support means being tiltable about said axis between a head-high position and a head-low position;
   (d) a removable longitudinally extending essentially radiolucent table top for medical imaging purposes, said table top being adapted to be detachably secured to said support means and to tilt longitudinally with said support member when secured thereto, at least a portion of said table top being directly above said base when secured to said support means, whereby 360° access to said table top is afforded; and
   (e) securing means for detachably securing said table top to said support means.

2. Apparatus according to claim 1 in which said table top is a member of a set of at least two interchangeable table tops, each of which is essentially radiolucent.

3. Apparatus according to claim 1 in which:
   (a) said first and second column members are first and second hollow housing members, respectively, of generally rectangular cross section and
   (b) said table-top support means comprises a pair of spaced vertically corotating pivot arms mounted on opposite sides of said second housing member, and a longitudinally extending support plate affixed to and rotatable with said pivot arms, wherein each said pivot arm comprises a longitudinally extending upper portion for supporting said support plate and a generally U-shaped portion depending therefrom, said transverse axis passes through said U-shaped portion, and said support plate is adapted to support said essentially radiolucent plate.

4. Apparatus according to claim 3 in which each of said pivot arms has an inwardly extending hinge pin, each said hinge pin extending inwardly from an end of a longitudinally extending upper portion of a pivot arm, the hinge pins of the respective pivot arms being coaxial and in which said securing means comprises a pair of opposed hinge blocks mounted on an underside of said table top, each hinge block having a receptacle for receiving a hinge pin, and a pair of locking blocks which are longitudinally spaced from respective hinge blocks, each locking block having associated therewith a plunger pin which is movable between an extended position and a retracted position, said plunger pin in its extended position engaging said support plate so as to secure the table top to the support plate.

5. Apparatus according to claim 1 in which said base is generally rectangular in shape.

6. Apparatus according to claim 1 in which said first and second column members are, respectively, a first hollow housing member affixed to said base, and a second hollow housing member, said first and second housing members being arranged in telescoping relationship.

7. Apparatus according to claim 1 in which said table top support means comprises a pair of spaced vertical a coaxial and co-rotating pivot arms which are pivotally mounted for rotation about said transverse axis, and a support plate affixed to and positioned above said pivot arms, whereby said support plate rotates with said pivot arms.

8. Apparatus according to claim 7 in which said first and second column members are first and second hollow housing members, respectively, of generally rectangular cross section and in which said pivot arms are pivotally mounted on opposite sides of said second housing member.

9. Apparatus according to claim 7, further including motorized drive means for causing said pivot arms to rotate about said transverse axis.

10. Apparatus according to claim 7 in which said pivot arms have coplanar upper support surfaces and said support plate is supported on said support surfaces.

11. Apparatus according to claim 7, further including a limit stop affixed to at least one pivot arm and solenoid operated mechanical stop means movable between a limit stop engaging position, and a solenoid, said mechanical stop means being in said limit stop engaging position when said solenoid is deenergized and in said limit stop disengaging position when said solenoid is energized.

12. Apparatus according to claim 11, wherein said mechanical stop means comprises a swingable arm and a link pivotally connected thereto, said swingable arm being swingable between a limit stop engaging position and a limit stop disengaging position, said solenoid including a solenoid body, a plunger reciprocable in said body and having one end extending outside said body, said plunger being connected at said one end to said link, and a compression spring which biases said plunger and said mechanical stop means to said limit stop engaging position, whereby said mechanical stop means is in said limit stop engaging position when said solenoid is deenergized and in said limit stop disengaging means when said solenoid is energized.

13. Apparatus for supporting a patient for medical diagnostic imaging purposes, said apparatus comprising:
   (a) a base supported on casters whereby the apparatus is mobile;
   (b) a column extending upwardly from said base, said column comprising a first column member affixed to said base and a second column member which is vertically reciprocable relative to said first member;
   (c) longitudinally tiltable table top support means for supporting a removable table top in a position such that at least a portion of said table top is directly above said base, said table top support means being supported by said second column member and reciprocable therewith, said support means being pivotally mounted on a transverse axis which passes directly above said base and through said second column member, said support means being tiltable between a head-high and a head-low position;
   (d) a set of interchangeable longitudinally extending table tops for medical imaging purposes, and set comprising at least two table tops, each said table top being adapted to be detachably secured to said support means and to tilt longitudinally with said support member when secured thereto, at least a portion of said table top being directly above said base when secured to said support means, whereby 360° access to said table top is afforded; and (e) securing means associated with each table top for securing said table top to said support means.

14. Apparatus for medical diagnostic imaging, said apparatus including longitudinally tiltable support means including a pair of spaced pivot arms for supporting a table top, said pivot arms being pivotally mounted for rotation about a transverse horizontal axis between a head-high and a head-low position;

said apparatus further including at least one limit stop affixed to at least one pivot arm of said support means, solenoid operative mechanical stop means movable between a limit stop engaging position and a limit stop disengaging position; and a solenoid, said solenoid including a solenoid body, a plunger reciprocable in said body and having one end extending outside said body said plunger being connected at said one end to said mechanical stop means, and a compression spring for biasing said plunger and said mechanical stop means to said limit stop engaging position, whereby said mechanical stop means is in said limit stop engaging position when said solenoid is deenergized and in said limit stop disengaging position when said solenoid is energized.

15. Apparatus according to claim 14 wherein said tiltable support means includes a pair of spaced vertical pivot arms and a limit stop is affixed to at least one of said pivot arms.

16. Apparatus according to claim 14, wherein said mechanical stop-means comprises a swingable arm and a link pivotally connected thereto, said swingable arm being swingable between a limit stop engaging position and a limit stop disengaging position, said plunger being connected at said one end to said link.

* * * * *